United States Patent [19]

Mosier

[11] Patent Number: 4,492,720

[45] Date of Patent: Jan. 8, 1985

[54] METHOD OF PREPARING MICROSPHERES FOR INTRAVASCULAR DELIVERY

[76] Inventor: Benjamin Mosier, 5139 S. Braeswood, Houston, Tex. 77096

[21] Appl. No.: 552,160

[22] Filed: Nov. 15, 1983

[51] Int. Cl.³ .............................................. B01J 13/02
[52] U.S. Cl. ................................. 427/213.3; 264/4.6; 424/22; 424/38
[58] Field of Search ...................... 264/4, 4.1, 4.4, 4.6, 264/4.7; 427/213.3; 252/315.01, 315.1, 315.3, 315.4; 604/890, 891; 424/19–22, 38

[56] References Cited

U.S. PATENT DOCUMENTS

| | | | |
|---|---|---|---|
| 3,880,991 | 4/1975 | Yolles | 604/891 |
| 3,891,570 | 6/1975 | Fukushima et al. | 264/4 |
| 3,943,063 | 3/1976 | Morishita et al. | 264/4.1 |
| 4,016,099 | 4/1977 | Wellman et al. | 264/4.1 |
| 4,107,288 | 8/1978 | Oppenheim et al. | 264/4.6 |
| 4,187,194 | 2/1980 | Wellman et al. | 264/4 |
| 4,230,687 | 10/1980 | Sair et al. | 264/4.6 |

Primary Examiner—Ben R. Padgett
Assistant Examiner—T. J. Wallen

[57] ABSTRACT

The field of this invention is the encapsulation of therapeutic or diagnostic substances in minute capsules or spheres from which the substances are slowly released over a prescribed period of time. The general processes for preparing such capsules or spheres include coacervation or a related process by means of which liquid droplets can be encapsulated, and solid phase entrapment in which the water-soluble agent is dispersed in a solid matrix material. The method of this invention can be classified as an improved procedure for matrix encapsulation or entrapment.

18 Claims, No Drawings

1

METHOD OF PREPARING MICROSPHERES FOR INTRAVASCULAR DELIVERY

BACKGROUND AND PRIOR ART

"Chemoembolization", the intraarterial delivery of chemotherapeutic agents in particulate form is a procedure which has recently been used both experimentally and in clinical practice: e.g., Kato et al. (1981), *A* 245 (11): 1123–1127; and Soo and Wallace (1982), *diovasc. Intervent. Radiol.* 5: 260–263. For this purpose, microspheres in the approximate size range of 50–300 microns are advantageous. The microspheres are introduced as a slurry into an artery supplying neoplasmic aggregate in the peripheral branches, and form a temporary or permanent blockage of the blood flow. The chemotherapeutic agent is thereby concentrated at the desired site. The release rate may be controlled by the character of the matrix material.

The methods for forming microspheres of below 5 microns in size, i.e. 0.5 to 1 micron, is presented; heretofore there has not been a commercially satisfactory procedure for conveniently and consistently producing microspheres in this size range for intravenous delivery. Such a process is especially needed for the controlled, prolonged release of almost any pharmaceutic agent. By concentrating the drug release at the site of the tumor, the effectiveness of the drug can be greatly enhanced while minimizing the undesirable side effects.

The patent art relating to the preparation of liquid-center microspheres, particularly by the technique of coacervation, is voluminous. The patent art of entrapment encapsulation is much less extensive. Further, no patent or other prior art directly relevant to the method of this invention is known. However, the following patents are believed to be illustrative of the general art of entrapment encapsulation to produce solid microspheres.

U.S. Patents

Yoshihito et al, U.S. Pat. No. 3,891,570 (1975)
Zolle, U.S. Pat. No. 3,937,668 (1976)
Morishita et al, U.S. Pat. No. 3,960,757 (1973)
Jaffe, U.S. Pat. No. 4,272,398 (1981)
Widder et al, U.S. Pat. No. 4,345,588 (1982)
Shasha, U.S. Pat. No. 4,382,813 (1983)

SUMMARY OF INVENTION

This invention is based on the discovery of an effective process for preparing solid microspheres containing releasable therapeutic or diagnostic agents of a size adapted for intraarterial delivery. Microspheres of this character having sizes in the range of 50 to 350 microns can be readily and consistently prepared. The resulting microspheres can therefore be used for administration of therapeutic or diagnostic agents, and the localization of the agent at the desired delivery site by the technique of embolization. A wide variety of non-toxic matrix materials can be employed, such as long chain fatty acid mono-, di-, and triglycerides. The method is adaptable to the encapsulation entrapment of any water-soluble therapeutic or diagnostic agent. Further, the organic solvents employed in the process can be completely removed so that the microspheres comprise essentially the matrix material with the water-soluble agent distributed therein. Further advantages of the process are that no unusual or special apparatus is required, and that the temperature conditions used, although important for optimized results are not ones requiring extensive heating or cooling. Further, microspheres can be obtained in a solid dry form, which at room temperatures or normal use temperatures can be relatively non-sticky and free-flowing.

DETAILED DESCRIPTION

In general, the method of this invention for preparing microspheres containing water-soluble therapeutic or diagnostic agents comprises a controlled sequence of steps. In the first step of the method, a solution is prepared by dissolving the water-soluble agent and the matrix material in an organic solvent in which they are mutually soluble. In certain embodiments, the agent may be substantially water-insoluble providing that it is soluble in the first solvent. The matrix material is heat-liquifiable at an elevated temperature, and the organic solvent is one having a relatively high dielectric constant. The prepared solution is dispersed in a second organic solvent to form an emulsion containing dispersed droplets of the solution, the second solvent forming a continuous phase. The second solvent has a low dielectric constant and is present in at least as great a volume as the solution. After forming the dispersion with the droplets of the desired size, substantially all of both of the solvents are removed from the dispersion while maintaining the droplets at a temperature substantially below the congealing temperature of the matrix material. This produces solid microspheres comprising the matrix material with the therapeutic or diagnostic agent distributed therein. The microspheres are recovered and used for delivery.

In preferred embodiments, a water-soluble anti-cancer agent such as floxuridine is encapsulated. A wide variety of other anti-cancer agents can be used such as Adriamycin (doxorubicin hydrochloride), vindesin, methotraxate, fluorouracil, 6-mercaptoprine, vinblastin, vincrastin, mitomycin C, actinomycin D, bleomycin, mithramycin, methanesulfon-M-anisidide, daunomycin, hydrochloride, medroxyprogesterone acetate, cis, dichlorodiaminine platinum (II), dacarbazine, and Corynbacterium parvum. The diagnostic agents may include contrast agents for X-ray examinations, such as bismuth sodium tartrate or sodium iodide, ferric cacodylet, iodinated ethyl ester of poppyseed oil, methyl glucamine diatrizoate (Renografin 60), acetyl hydroxamic acid, etc. See Young, et al (1981), Radiology 138: 97–105.

The matrix material is preferably selected so that it is non-toxic under the conditions of administration. It should be a heat-liquifiable material having congealing temperatures above 100° F. and preferably above 125° F. The term "congealing temperature" refers to the temperature or temperature range at which the phase change from liquid to solid occurs. Typically, the matrix material will have a congealing temperature in the range from about 125° to 165° F. Substances such as high melting waxes may be used with congealing temperatures as high as 200°–250° F. Another important characteristic of the matrix material is that it should be soluble in non-polar, high dielectric-type organic solvents. In preferred embodiments, the matrix material is biodegradable. However, where it is desired to create a permanent embolus, a non-biodegradable matrix material may be used.

One preferred class of matrix materials are the fatty acid glycerides, such as the mono-, di-, and triglycerides of long chain fatty acids. The glycerides may therefore contain from 1 to 3 fatty acid groups and the fatty acid groups may contain from 12 to 22 carbons. Particularly desirable are the fatty acid monoglycerides including acetylated monoglycerides (viz. glycerol monostearate) containing from 12 to 18 carbons such as steryl or palmityl monoglycerides. Another related class of desirable matrix materials comprises propylene glycol monoesters of fatty acids in which the fatty acid groups contain predominantly from 12 to 18 carbons. Such fatty acid monoglycerides and propylene glycol monoesters are sold under the name "Myverol" by DPI Division, Eastman Chemical Products, Inc., Kingsport, Tenn.

Other suitable matrix materials include fatty acids ($C_{10}$–$C_{16}$), guar gums (hydroxy propyl), Vitamin A palmitate, lecithin and other natural phospholipids, cholesterol and fatty acid esters thereof such as cholesterol, palmitate, plant sterols, including sitosterol, stigmasterol, and phytosterol, tocopherol succinate, cellulose derivatives which are soluble in non-polar organic solvents such as methyl cellulose and hydroxyethyl cellulose, propyl cellulose, nitrocellulose, polyvinyl pyrrolidone, polyvinyl alcohols, vegetable protein materials, such as zein (prolamine), poly d, l lactides which are soluble in polar or high dielectric organic solvents, as well as waxes having such solubility characteristics including natural and synthetic waxes (e.g. ethylene bis-stearamide), castorwax, cetyl stearyl alcohol, microcrystalline wax, etc. It is an advantage of the method of this invention that a wide variety of matrix materials may be employed while using the basic process.

The organic solvent in which the water-soluble therapeutic or diagnostic agent is dissolved together with the matrix material should be selected so it has a relatively high dielectric constant. In general, organic solvents having dielectric constants above 15, such as dielectric constants in the range of 20 to 40, are suitable. Such solvents include the lower alcohols like methanol, ethanol, and isopropanol, the lower ketones such as acetone, and similar solvents of high dielectric constants such as dioxane, tetrahydrofuran, acetonitrile, etc. These solvents are generally classified as polar-type organic solvents, being miscible with water and, in general, having a solubilizing action similar to that of water.

The therapeutic or diagnostic agent may be dissolved in the first solvent to increase its solubility limit at the temperatures to be employed in the process. Thus, depending on the particular high dielectric solvent and the particular water-soluble agent, the resulting solution may contain from 5 to 95% by weight of the water-soluble agent based on the weight of the solution. More typically, however, the solution will contain from 25 to 75% by weight of the agent. It is desirable to employ relatively high concentrations of the agent in the first solvent, thereby providing concentrated solutions for use in the method of this invention.

The second organic solvent used in the process is of the non-polar, low dielectric type. In general, the second solvent will have a dielectric constant below 5, such as a constant in the range from 1 to 3. The second solvent should be selected so that it is immiscible with the first solvent, which, in general, is a property of the non-polar type organic solvents relative to the polar organic solvents. Preferably, the second solvent is substantially completely immiscible in the first solvent. The partition coefficient between the solvents will therefore be low. Examples of suitable second solvents are petroleum ether, benzene, hexane, heptane or cyclohexane, etc. Other suitable second solvents can be readily selected in relation to the first solvent and the objectives of this invention.

In carrying out the method of this invention, the prepared solution of the water-soluble agent in the high dielectric organic solvent is dispersed in the second organic solvent to form an emulsion containing dispersed droplets of the solution, the second solvent being the continuous phase of the emulsion. Various techniques may be employed to promote the dispersion and form an emulsion of finely dispersed droplets. For example, the first solution may be introduced into the second solvent in droplet form, such as by dripping or spraying, and/or the application of fine mixing techniques to the emulsion, such as sonification or high speed shear mixing. The objective is to produce a fine dispersion in which the droplets of the first solution have average sizes in the range up to about 200 microns, typically above 25 microns such as from about 50 to 150 microns. Smaller size microspheres can also be produced down to 1 to 10 microns. The formulation of the emulsion and the stability of the emulsion after forming may be promoted by the use of suitable surface active agents. For present purposes, such surface active agents include ethoxylated sorbitan monooleate, and similar emulsifying agents, such as sorbitan monooleate containing from 5 to 20 moles of ethylene oxide.

The second solvent should be used in at least as great a volume as the solution being dispersed in it. For example, the volume ratio of the solution to the second solvent may range from 1:1 to 1:8. An advantageous range on the same basis is usually from about 1:2 to 1:6.

To facilitate their removal in the next step of the process, both the first and second solvents should be volatile solvents, that is, in general they should have atmospheric boiling points substantially below the congealing temperature of the matrix material (e.g. 25° F. or more below). Very high boiling solvents are undesirable since it will be difficult to remove them while maintaining the microspheres in solid form.

Temperature controls are preferably exercised throughout the process. In forming the solution, ordinary room temperatures are desirable, such as temperatures from 60° to 90° F. The temperature at which the solution is formed should be below the boiling point of the first solvent at atmospheric pressure and, preferably at a temperature below the congealing temperature of the matrix material. In some cases, however, it may be desirable to employ a dissolving temperature above the congealing temperature of the matrix material to promote its rapid dissolution. The second solvent into which the solution is dispersed should be maintained at a temperature substantially below the congealing temperature of the matrix material. Preferably the second solvent is at a temperature below 50° C. when the dispersion is being formed, such as a temperature in the range of 5° to 30° C. It is particularly important to have the dispersion at a relatively low temperature during the solvent removal steps. This assures that the matrix material will be in a solid form, which is relatively non-sticky and non-aggregating so that the microspheres can be obtained as separate microspheres of the desired size.

In one preferred solvent removal procedure, the dispersion is processed at a temperature of 0° to 30° F., such as preferably around 10° to 20° F., and the major portion of the second solvent is removed first. Filtration or decanting can be used. For example, this can be accomplished by permitting the formed microspheres to settle and decanting the second solvent. Alternatively, separation of the microspheres from the second solvent can be carried out by filtration or centrifugation. Following removal of a major portion of the second solvent, the remaining portion of the second solvent and the first solvent can be removed by evaporation under reduced pressure. The evaporation temperature employed should be well below the congealing temperature of the matrix material, as previously described.

After substantially all of both solvents are removed under the specified temperature conditions, the resulting microspheres are recovered in solid form, the water-soluble agent being distributed in the solidified matrix material. The recovered microspheres of average sizes in the range of 50 to 350 microns may be stored in solid form, preferably under refrigeration in the solid form, or may be redispersed in a suitable physiological liquid carrier, such as an aqueous solution (viz. normal saline, Ringer's solution, etc.). The viscosity of the aqueous solution may be increased by a viscosifier such as dextran, polyvinyl, pyrollidone, natural gums, etc. It will be understood that the redispersions should be prepared in sterile form for intraarterial administration, and that they should be free of substances which are not accepted for such administration.

The method of this invention is further illustrated by the following examples.

EXAMPLE I

The matrix material was Myverol 18-00, a hydrogenated lard having an approximate congealing point of 154° F. (DPI Division, Eastman Chemical Products, Inc., Kingsport, Tenn.). The first solvent was a mixture of equal parts by volume of tetrahydrofuran and methanol, 3 grams of the Myverol being dissolved per 40 cc of the solvent mixture. The chemotherapeutic agent, FUDR (floxuridine) was dissolved in tetrahydrofuran, 1.5 gm being dissolved in 10 cc. The solution of the chemotherapeutic agent was mixed with the matrix-solvent solution in the proportions of about 10 cc of the chemotherapeutic agent solution per 40 cc of the matrix solution. The temperature of the combined mixture was at room temperature (70°-80° F.). Droplets of the mixture were introduced into a beaker containing 300 cc of petroleum ether with 1% by weight each of sorbitan monooleates containing, respectively, 5 and 20 moles of ethylene oxide. The solution of the chemotherapeutic agent and matrix material was introduced dropwise into the second solvent containing the surface active agent while sonication was continously applied (viz. at a level of 20 KHz). On completion of the addition of the prepared solution, sonication was continued for approximately another 5 minutes. This completed the dispersion of the prepared solution in the second organic solvent, forming an emulsion containing finely dispersed droplets of the prepared solution in the second solvent.

The microspheres thus prepared can be recovered by one of several procedures. They may be recovered on a filter, or they can be separated from the solvent by spray drying. During recovery, the temperature is maintained well below the congealing temperature of the Myverol, such as a temperature of around 35° F. Residual second solvent and the first solvent can be removed from the filter-recovered microspheres by vacuum drying.

The average size of the recovered microspheres was in the range from 106 to 149 microns, the microspheres containing about 30–35% active chemotherapeutic agent. The rate of release of the drug was tested in dog's blood at room temperature (viz. about 75° F.). The data is summarized below in Table A.

TABLE A

| Time (hrs.) | Cumulative Release (% by Wt.) |
|---|---|
| 0.5 | 23.8 |
| 1.0 | 37.5 |
| 1.5 | 69.6 |
| 2.0 | 85.7 |
| 2.5 | 90.1 |
| 3.0 | 96.1 |

Following the procedure described above, the same drug was encapsulated at a lower concentration to give microspheres of about 12.5% active content. These were tested for release rate by the same procedure. The results are summarized below in Table B.

TABLE B

| Time (hrs.) | Cumulative Release (% by Wt.) |
|---|---|
| 0.5 | 18.3 |
| 1.0 | 41.2 |
| 1.5 | 59.9 |
| 2.0 | 78.4 |
| 2.5 | 88.8 |
| 3.0 | 96.7 |

EXAMPLE II

Microspheres were prepared according to the procedure of Example I except that the matrix material was a mixture of 2 gms. Myverol 18-06 (hydrogenated vegetable oil having an approximate congealing point of 156° F.) with 0.5 gm unmodified soya lecithin. 2.5 gms of FUDR was combined with the 2.5 gms of the matrix mixture, and the microspheres were formed in the same manner at a temperature of about 32° F. They were recovered by filtration, the residual second solvent and the first solvent being removed by vacuum evaporation. Using dog's blood as the test medium at room temperature, the release rate was studied over 6 hours, the data being summarized below in Table C.

TABLE C

| Time (hrs.) | Cumulative Release (% by Wt.) |
|---|---|
| 0.5 | 7.9 |
| 1.0 | 28.0 |
| 1.5 | 35.9 |
| 2.0 | 40.7 |
| 2.5 | 61.8 |
| 3.0 | 68.3 |
| 3.5 | 73.1 |
| 4.0 | 78.2 |
| 4.5 | 84.0 |
| 5.0 | 89.1 |
| 6.0 | 94.4 |

EXAMPLE III

This example illustrates the encapsulation of an iodinated radiographic contrast agent (Renografin 60). The procedure was generally the same as that described in Example I. 5 gms of the dry contrast agent was dissolved in 100 cc absolute ethanol. 2.5 gm of ethyl hydroxyethylcellulose (EHEC) was dissolved in 50 cc of the absolute ethanol. The EHEC was of the low viscosity type having a viscosity of 20–30 centiposes in a 5% ethanol solution. The two ethanol solutions were combined and added to 350 cc of petroleum ether as described in Example I. The temperature was kept below 40° F. Microspheres of 5–50 microns were obtained. The first and second solvents were evaporated by passing cold nitrogen vapor over the microsphere dispersion while stirring. The recovered microspheres were redispersed in 100 cc of Ringer's solution.

EXAMPLE IV

As a variation of the procedure of Example I, the first solvent was a mixture of benzene and tetrahydrofuran (THF), 2 gms of FUDR was dissolved in 40 cc THF, which was mixed with 10 cc of benzene containing 3 grams of poly-d,l-lactide, as the matrix material. The prepared solution was then introduced into petroleum ether, the procedure being generally the same as in Example I. The microspheres were recovered on a filter and the solvent removed as described in Example I. The microsphere size range was from 106 to 149 microns.

EXAMPLE V

Following the general procedure of Example I, 2 gms of acetyl hydroxamic acid (AHA) was dissolved in 5 cc methanol and added to 20 cc tetrahydrofuran (THF). One gram of Myverol 18-06 was added in 20 cc THF to complete preparation of the mixture. The completed mixture was introduced into cold heptane (viz. 35° F.) dropwise accompanied by sonication. The heptane contained the same surface active agents as in Example I. The recovered microspheres had a size range from about 75 to 149 microns.

EXAMPLE VI

Citric acid was encapsulated by dissolving 1 gm in 50 cc absolute ethanol in admixture with 2 cc water. The matrix material was the same as identified in Example III (EHEC), being added in the amount of 1 gm to a mixture of 20 cc ethanol with 20 cc tetrahydrofuran. The mixture was introduced dropwise with sonication into n-hexane using the same surfactant system as the prior examples. The micro-spheres were recovered by filtration and vacuum drying, giving microspheres of a size range of 106–149 microns. The temperature during forming of the microspheres and their recovery was maintained around 35° F.

EXAMPLE VII

This example illustrates the encapsulation of a non-water soluble material, Ethiodol, which is the ethyl ester of poppyseed oil that has been iodinated for use as a contrast agent. 10 cc of the Ethiodol concentrate was dissolved in 35 cc of tetrahydrofuran (THF). The matrix material was the EHEC material of Example III, 2 gms being dissolved in 25 cc THF. The mixture was introduced into cold petroleum ether (35° F.) containing 1% ethoxylated cetyl ether (Volpo 5, Croda). After formation of the microsphere dispersion, using the procedure of Example I, the volume of the dispersion was reduced by blowing cold nitrogen over the stirred dispersion. This removes substantially all of the petroleum ether and THF, resulting in a reduced volume of about 100 cc. The microsphere concentrate was dispersed in 100 cc of Ringer's solution. The residual THF and petroleum ether were removed by subjecting the redispersion to vacuum evaporation. The microspheres ranged in size from 1 to 10 microns.

EXAMPLE VIII

The procedure of Example VII is followed except an auxillary coating is incorporated into the Ringer's or normal saline solution. Some representative biocompatible materials which have been demonstrated to be effective are 1% solutions of collagen, isoelectric gelatins A & B, hemoglobin, albumin, pectin, etc. The resulting microspheres range in size from 1 to 25 microns.

I claim:

1. The method of preparing microspheres containing therapeutic or diagnostic agents, comprising:
   (a) preparing a solution by dissolving said agent and a non-toxic matrix material in a first organic solvent in which they are mutually soluble, said matrix material being heat-liquifiable and having a congealing temperature above 100° F., said first organic solvent having a dielectric constant above 15;
   (b) dispersing the prepared solution in a second organic solvent to form an emulsion containing dispersed droplets of said solution in said second solvent as the continuous phase, said second organic solvent having a dielectric constant below 5, and being present in at least as great a volume as said solution;
   (c) removing substantially all of both of said solvents from said dispersion while maintaining said droplets at a temperature substantially below the congealing temperature of said matrix material to produce solid microspheres comprising said matrix material with said water-soluble agent distributed therein; and
   (d) recovering said microspheres.

2. The method of claim 1 in which said matrix material is composed primarily of fatty acid glycerides in which the glycerides contain from 1 to 3 fatty acid groups and the fatty acid groups contains from 12 to 22 carbons.

3. The method of claim 1 in which said matrix material is composed primarily of fatty acid monoglycerides in which the fatty acid groups contain predominately from 12 to 18 carbons.

4. The method of claim 1 in which said matrix material is composed primarily of propylene glycol monoesters of fatty acids in which the fatty acid groups contain predominately from 12 to 18 carbons.

5. The method of claim 1 in which said first solvent has a dielectric content in the range from 20 to 40.

6. The method of claim 1 in which said second solvent has a dielectric constant in the range from 1 to 3.

7. The method of claim 1 in which said second solvent is present in the volume ratio of from 2 to 4 parts per part of said prepared solution.

8. The method of claim 1 in which said dispersion is at a temperature in the range of 0° to 50° F. when the removal of said solvents is begun, and said droplets are maintained at a temperature below 50° F. while said solvents are being removed.

9. The method of claim 1 in which said prepared solution is formed at a temperature of from 60° to 90° F., said second solvent is at a temperature below 50° F. when said dispersion is prepared, and said droplets are maintained at a temperature below 50° F. while said solvents are being removed.

10. The method of claim 1 in which the first step in removing said solvents is the separation of said droplets from most of said second solvent by mechanical separation, and in which the rest of said second solvent and said first solvent are removed by evaporation under reduced pressure.

11. The method of preparing microspheres containing water-soluble anti-cancer agents for intravascular delivery, comprising:
  (a) preparing a solution by dissolving the water-soluble anti-cancer agent and a non-toxic biodegradable matrix material in a first organic solvent in which they are mutually soluble, said matrix material being heat-liquifiable and having a congealing temperature above 125° F., said first organic solvent having a dielectric constant in the range from 20 to 40;
  (b) dispersing the prepared solution in a second organic solvent to form an emulsion containing finely dispersed droplets of said solution in said second solvent as the continuous phase, said second solvent having a dielectric constant in the range from 1 to 3;
  (c) removing substantially all of both of said solvents from said dispersion while maintaining said droplets at a temperature substantially below the congealing temperature of said matrix material to produce solid microspheres comprising said matrix material with said anti-cancer agent distributed therein; and
  (d) recovering said microspheres.

12. The method of claim 11 in which said matrix material is selected from the class consisting of fatty acid esters of glycerin or proplyene glycol having from 1 to 3 fatty acid groups containing from 12 to 18 carbon atoms.

13. The method of claim 11 in which said dispersion is at a temperature below 50° F. and when the removal of said solvents is begun, and said droplets are maintained at a temperature below 50° F. while said solvents are being removed.

14. The method of claim 11 in which said prepared solution is formed at a temperature of from 60° to 90° F., said second solvent is at a temperature below 50° F. when said dispersion is prepared, and said droplets are maintained at a temperature below 50° F. while said solvents are being removed.

15. The method of claim 11 in which the first step in removing said solvents is the separation of said droplets from most of said second solvent by mechanical separation, and in which the rest of said second solvent and said first solvent are removed by evaporation under reduced pressure.

16. The method of claim 11 in which the recovered microspheres have an average size of from 50 to 200 microns, said recovered microspheres being adapted for intravascular administration and localization.

17. The method of preparing microspheres containing water-soluble therapeutic or diagnostic agents, comprising:
  (a) preparing a solution by dissolving said water-soluble agent and a non-toxic biodegradable matrix material in a first organic solvent in which they are mutually soluble, said solution being formed at a temperature in the range from 60° to 90° F., said matrix material being heat-liquifiable and having a congealing temperature above 125° F. said first organic solvent having a dielectric constant in the range from 20 to 40;
  (b) dispersing the prepared solution in a second organic solvent at a temperature below 40° F. to form an emulsion containing finely dispersed droplets of said solution in said second solvent as the continuous phase, said second solvent having a dielectric constant in the range from 1 to 3 and being present in from 2 to 4 parts by volume per part of said solution;
  (c) while said droplets are maintained in said second solution at a temperature of from 5° to 50° F. removing substantially all of both of said solvents from said dispersion to produce solid microspheres comprising said matrix material with said agent distributed therein; and
  (d) recovering said microspheres.

18. The method of claim 17 in which the recovered microspheres have an average size of from 50 to 200 microns, said recovered microspheres being adapted for intravascular administration and localization.

* * * * *